United States Patent
Shanklin et al.

(10) Patent No.: US 10,351,868 B2
(45) Date of Patent: Jul. 16, 2019

(54) ENGINEERING CYCLOPROPANE FATTY ACID ACCUMULATION IN PLANTS

(71) Applicant: Brookhaven Science Associates, LLC, Upton, NY (US)

(72) Inventors: John Shanklin, Shoreham, NY (US); Xiao-Hong Yu, Mount Sinai, NY (US); Richa Rawat Prakash, Medford, NY (US)

(73) Assignee: Brookhaven Science Associates, LLC, Upton, NY (US)

(*) Notice: Subject to any disclaimer, the term of this patent is extended or adjusted under 35 U.S.C. 154(b) by 424 days.

(21) Appl. No.: 14/914,532

(22) PCT Filed: Aug. 26, 2014

(86) PCT No.: PCT/US2014/052668
§ 371 (c)(1),
(2) Date: Feb. 25, 2016

(87) PCT Pub. No.: WO2015/031335
PCT Pub. Date: Mar. 5, 2015

(65) Prior Publication Data
US 2016/0222398 A1  Aug. 4, 2016

Related U.S. Application Data

(60) Provisional application No. 61/870,819, filed on Aug. 28, 2013.

(51) Int. Cl.
*C12N 15/82* (2006.01)
*C12P 7/64* (2006.01)
*C12N 9/10* (2006.01)

(52) U.S. Cl.
CPC ....... *C12N 15/8247* (2013.01); *C12N 9/1007* (2013.01); *C12P 7/6409* (2013.01); *C12P 7/6463* (2013.01)

(58) Field of Classification Search
None
See application file for complete search history.

(56) References Cited

U.S. PATENT DOCUMENTS

| | | |
|---|---|---|
| 5,936,139 A | 8/1999 | Schmid |
| 6,855,863 B1 | 2/2005 | Cahoon et al. |
| 7,446,188 B2 | 11/2008 | Bao et al. |
| 7,608,443 B2 | 10/2009 | Kinney et al. |
| 7,723,574 B2 | 5/2010 | Zank et al. |
| 7,855,321 B2 | 12/2010 | Renz et al. |
| 8,101,818 B2 | 1/2012 | Browse et al. |
| 8,110,388 B2 | 2/2012 | Ochiai et al. |
| 8,354,569 B2 | 1/2013 | Renz et al. |
| 8,383,886 B2 | 2/2013 | Chen et al. |

FOREIGN PATENT DOCUMENTS

| | | |
|---|---|---|
| WO | 2003060079 A2 | 7/2003 |
| WO | 2007141257 A1 | 12/2007 |

OTHER PUBLICATIONS

Burgal et al 2008 (Plant Biotechnology Journal 6: p. 819-831).*
Wang et al Biochemistry 31:45 p. 11020-11028).*
Dubois et al 2007 (Eur J Lipid Sci Technol 109: p. 710-732).*
Yu, X-H., "Enhancing Cyclopropane Fatty Acid Production in Plants," dated Feb. 25, 2013, Microsoft Power Point Slides.
Yu, X-H., "Coexpressing *Escherichia coli* Cyclopropane Synthase with Sterculia foetida Lysophosphatidic Acid Acyltransferase Enhances Cyclopropane Fatty Acid Accumulation," Plant Physiology, vol. 164, pp. 455-465 (2014).
Winichayakul, S., et al., "Delivery of grasses with high levels of unsaturated, protected fatty acids," Proceedings of the New Zealand Grassland Association 70:211-216 (2008).
Bates, P. D., et al., "The significance of different diacylglycerol synthesis pathways on plant oil composition and bioengineering," Frontiers in Plant Science/Plant Metabolism and Chemodiversity, , vol. 3, Article 147, pp. 1-11 (2012).
Mputu, M. N., et al., "Identification of a potential bottleneck in branched chain fatty acid incorporation into triacylglycerol for lipid biosynthesis in agronomic plants," Biochimie, vol. 91(6):703-710 (2009).
Zou, J., et al., "Modification of Seed Oil Content and Acyl Composition in the Brassicaceae by Expression of a Yeast sn-2 Acyltransferase Gene," Plant Cell., vol. 9(6):909-923 (1997).
Schultz, D. J., "Expression of a Δ9 14:0-acyl carrier protein fatty acid desaturase gene is necessary for the production of ω5 anacardic acids found in pest-resistant geranium (*Pelargonium xhortorum*)," Plant Biology, Proc. Natl. Acad. Sci. USA, vol. 93, pp. 8771-8775 (1996).
Meesapyodsuk, D., "An Oleate Hydroxylase from the Fungus *Claviceps purpurea*: Cloning, Functional Analysis, and Expression in *Arabidopsis*[OA]," Plant Physiology, vol. 147, pp. 1325-1333 (2008).
Knutzon, D. S., "Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels," Plant Physiology, vol. 120, pp. 739-746 (1999).
Nguyen, H. T., et al., "Camelina seed transcriptome: a tool for meal and oil improvement and translational research," Plant Biotechnol J., 11(6), pp. 759-769 (2013).

(Continued)

*Primary Examiner* — Matthew R Keogh
(74) *Attorney, Agent, or Firm* — Dorene M. Price

(57) ABSTRACT

Heterologous expression of *E. coli* cyclopropane synthase in genotypic and phenotypic fad2fae1 plants facilitates accumulation of cyclopropane fatty acids. Co-expression of *Sterculia foetida* transferases, including lysophosphatidic acid acyltransferase, diacylglycerol acyltransferase (DGAT), and Phospholipid Diacyl Glycerol Acyltransferase (PDAT), with *E. coli* cyclopropane synthase further enhances cyclopropane fatty acid accumulation in fad2fae1 plant seeds.

8 Claims, 5 Drawing Sheets

Specification includes a Sequence Listing.

(56) References Cited

OTHER PUBLICATIONS

Napier, J. A., "The Production of Unusual Fatty Acids in Transgenic Plants," Annu. Rev. Plant Biol., 58:295-319 (2007).

Horn, P. J., et al., "Imaging heterogeneity of membrane and storage lipids in transgenic *Camelina sativa* seeds with altered fatty acid profiles," Plant J., 76(1):138-150 (2013).

Van Erp, H., et al., "Castor phospholipid:diacylglycerol acyltransferase facilitates efficient metabolism of hydroxy fatty acids in transgenic *Arabidopsis*," Plant Physiol., 155(2):683-693 (2011) and supplemental data pp. 1-7.

Kang, J., et al., "Identification of three genes encoding microsomal oleate desaturases (FAD2) from the oilseed crop *Camelina sativa*," Plant Physiol Biochem, 49(2):223-229 (2011).

Smith, M. A., "Heterologous expression of a fatty acid hydroxylase gene in developing seeds of *Arabidopsis thaliana*," Planta, 217(3):507-16 (2003).

Bao, X., et al., "Characterization of cyclopropane fatty-acid synthase from Sterculia foetida," J Biol Chem, vol. 278, No. 15, pp. 12846-12853 (2003).

Xu, X.-H., "Enhancing cyclopropane fatty acid production in plants," presentation slides, Feb. 25, 2013, pp. 1-20.

Bao, X., "Carbocyclic fatty acids in plants: biochemical and molecular genetic characterization of cyclopropane fatty acid synthesis of Sterculiafoetida," Proc Natl Acad Sci USA, vol. 99, No. 10, pp. 7172-7177 (2002).

Yu, X.-H., "Characterization and analysis of the cotton cyclopropane fatty acid synthase family and their contribution to cyclopropane fatty acid synthesis," BMC Plant Biol., 11:97 (2011).

Burgal, J., et al., "Metabolic engineering of hydroxy fatty acid production in plants: RcDGAT2 drives dramatic increases in ricinoleate levels in seed oil," Plant Biotechnol J., 6(8):819-31 (2008).

Yu, X.-H., et al. Coexpressing *Escherichia coli* Cyclopropane Synthase with Sterculia foetida "Lysophosphatidic Acid Acyltrasnferase Enahnces Cyclopropane Fatty Acid Accumulation," Plant Physiology., 164: 455-465 (2014).

* cited by examiner

ATGGCGATTGCAGCGGCAGCTGTCATCGTCCCACTTGGCCTTCTCTTCTTCATCTCTGGTCTCGTTGTCAATCTCATT
CAGGCAGTATGCTTTGTTCTCATTCGGCCACTGTCCAAGAAAACCTATAGAAAGATCAATAAGGTGGTTGCAGAGT
TGTTGTGGCTGGAACTCATATGGCTTGTTGATTGGTGGGCGGGAGTTAAGATTAAAGTGTTTGCAGATCATGAAA
GCTTCAATTTAATGGGTAAGGAACATGCCCTTGTTGTAGCCAATCACAGAAGTGATATTGATTGGTTAGTTGGATG
GGTTTTGGCTCAGCGATCTGGTTGTCTTGGAAGTTCAGTAGCTGTAATGAAGAAATCATCAAAATTCCTTCCGGTC
ATAGGTTGGTCAATGTGGTTTTCTGAGTATCTGTTTTTGGAACGAAACTGGGCCAAGGATGAAAGCACGCTAAAG
GCAGGCCTTCAACGTTTAAAGGACTTCCCACAGCCCTTTTGGTTGGCACTTTTTGTAGAAGGAACTCGCTTTACGCA
GGCAAAGCTTCTAGCAGCTCAAGAATATGCGACCTCACAAGGATTGCCTATACCTAGAAATGTTTTAATTCCTCGT
ACAAAGGGTTTTGTTTCAGCTGTAAGTCATATGCGTTCATTTGTCCCAGCCATTTATGATATGACAGTGGCTATTCC
AAAAAGCTCGCCTTCACCAACAATGCTTAGACTTTTCAAGGGGCAATCTTCTGTTGTGCATGTACACATCAAGCGG
CGTCTCATGAAGGAACTTCCTGAAACGGATGAGGCTGTTGCACAATGGTGTAAAGATATGTTTGTGGAGAAGGAC
AAGTTGTTGGACAAACATATTGCTGAGGACACTTTCAGTGACCAACCATTACACTATCTTGGTCGGCCAATTAAGC
CTCTTTTGGTTGTTACTTCTTGGGCATGCTTTGTGGCTTATGGAGCTCTCAAATTTCTGCAATGGTCTTCACTTTTATC
CTCATGGAAAGGGATTGCATTTTCAGCTTTTGGCTTGGCCATCGTTACCATCCTTATGCATATCTTGATACTCTTCTC
TCAGTCAGAGCGTTCAACTCCTGCCAAGGTTGCACCGGGGAAGCCCAAGAATGACCAGGAGAATTTGGAGGCAA
GACGAGACAAACAGCAGTAG

Fig. 3

SEQUENCE LISTING

```
<160> NUMBER OF SEQ ID NOS: 6

<210> SEQ ID NO 1
<211> LENGTH: 1164
<212> TYPE: DNA
<213> ORGANISM: Sterculia foetida
<220> FEATURE:
<221> NAME/KEY: misc_feature
<223> OTHER INFORMATION: S. foetida LPAT cDNA

<400> SEQUENCE: 1
atggcgattg cagcggcagc tgtcatcgtc ccacttggcc ttctcttctt catctctggt      60
ctcgttgtca atctcattca ggcagtatgc tttgttctca ttcggccact gtccaagaaa     120
acctatagaa agatcaataa ggtggttgca gagttgttgt ggctggaact catatggctt     180
gttgattggt gggcgggagt taagattaaa gtgtttgcag atcatgaaag cttcaattta     240
atgggtaagg aacatgccct tgttgtagcc aatcacagaa gtgatattga ttggttagtt     300
ggatgggttt tggctcagcg atctggttgt cttggaagtt cagtagctgt aatgaagaaa     360
tcatcaaaat tccttccggt cataggttgg tcaatgtggt tttctgagta tctgtttttg     420
gaacgaaact gggccaagga tgaaagcacg ctaaaggcag gccttcaacg tttaaaggac     480
ttcccacagc cctttggtt ggcactttt gtagaaggaa ctcgctttac gcaggcaaag     540
cttctagcag ctcaagaata tgcgacctca caaggattgc ctatacctag aaatgtttta     600
attcctcgta caaagggttt tgtttcagct gtaagtcata tgcgttcatt tgtcccagcc     660
atttatgata tgacagtggc tattccaaaa agctcgcctt caccaacaat gcttagactt     720
ttcaaggggc aatcttctgt tgtgcatgta cacatcaagc ggcgtctcat gaaggaactt     780
cctgaaacgg atgaggctgt tgcacaatgg tgtaaagata tgtttgtgga gaaggacaag     840
ttgttggaca aacatattgc tgaggacact ttcagtgacc aaccattaca ctatcttggt     900
cggccaatta agcctctttt ggttgttact tcttgggcat gctttgtggc ttatggagct     960
ctcaaatttc tgcaatggtc ttcactttta tcctcatgga aagggattgc attttcagct    1020
tttggcttgg ccatcgttac catccttatg catatcttga tactcttctc tcagtcagag    1080
cgttcaactc ctgccaaggt tgcaccgggg aagcccaaga tgaccagga gaatttggag    1140 gcaagacgag acaaacagca gtag                                           1164

<210> SEQ ID NO 2
<211> LENGTH: 387
<212> TYPE: PRT
<213> ORGANISM: Sterculia foetida
<220> FEATURE:
<221> NAME/KEY: misc_feature
<223> OTHER INFORMATION: S. foetida LPAT

<400> SEQUENCE: 2

Met Ala Ile Ala Ala Ala Ala Val Ile Val Pro Leu Gly Leu Leu Phe
1               5                   10                  15

Phe Ile Ser Gly Leu Val Val Asn Leu Ile Gln Ala Val Cys Phe Val
            20                  25                  30

Leu Ile Arg Pro Leu Ser Lys Lys Thr Tyr Arg Lys Ile Asn Lys Val
        35                  40                  45
```

Val Ala Glu Leu Leu Trp Leu Glu Leu Ile Trp Leu Val Asp Trp Trp
 50                  55                  60

Ala Gly Val Lys Ile Lys Val Phe Ala Asp His Glu Ser Phe Asn Leu
 65                  70                  75                  80

Met Gly Lys Glu His Ala Leu Val Val Ala Asn His Arg Ser Asp Ile
                 85                  90                  95

Asp Trp Leu Val Gly Trp Val Leu Ala Gln Arg Ser Gly Cys Leu Gly
                100                 105                 110

Ser Ser Val Ala Val Met Lys Lys Ser Ser Lys Phe Leu Pro Val Ile
            115                 120                 125

Gly Trp Ser Met Trp Phe Ser Glu Tyr Leu Phe Leu Glu Arg Asn Trp
130                 135                 140

Ala Lys Asp Glu Ser Thr Leu Lys Ala Gly Leu Gln Arg Leu Lys Asp
145                 150                 155                 160

Phe Pro Gln Pro Phe Trp Leu Ala Leu Phe Val Glu Gly Thr Arg Phe
                165                 170                 175

Thr Gln Ala Lys Leu Leu Ala Ala Gln Glu Tyr Ala Thr Ser Gln Gly
                180                 185                 190

Leu Pro Ile Pro Arg Asn Val Leu Ile Pro Arg Thr Lys Gly Phe Val
            195                 200                 205

Ser Ala Val Ser His Met Arg Ser Phe Val Pro Ala Ile Tyr Asp Met
210                 215                 220

Thr Val Ala Ile Pro Lys Ser Ser Pro Ser Pro Thr Met Leu Arg Leu
225                 230                 235                 240

Phe Lys Gly Gln Ser Ser Val Val His Val His Ile Lys Arg Arg Leu
                245                 250                 255

Met Lys Glu Leu Pro Glu Thr Asp Glu Ala Val Ala Gln Trp Cys Lys
                260                 265                 270

Asp Met Phe Val Glu Lys Asp Lys Leu Leu Asp Lys His Ile Ala Glu
            275                 280                 285

Asp Thr Phe Ser Asp Gln Pro Leu His Tyr Leu Gly Arg Pro Ile Lys
290                 295                 300

Pro Leu Leu Val Val Thr Ser Trp Ala Cys Phe Val Ala Tyr Gly Ala
305                 310                 315                 320

Leu Lys Phe Leu Gln Trp Ser Ser Leu Ser Ser Trp Lys Gly Ile
                325                 330                 335

Ala Phe Ser Ala Phe Gly Leu Ala Ile Val Thr Ile Leu Met His Ile
            340                 345                 350

Leu Ile Leu Phe Ser Gln Ser Glu Arg Ser Thr Pro Ala Lys Val Ala
            355                 360                 365

Pro Gly Lys Pro Lys Asn Asp Gln Glu Asn Leu Glu Ala Arg Arg Asp
     370                 375                 380

Lys Gln Gln
385

<210> SEQ ID NO 3
<211> LENGTH: 999
<212> TYPE: DNA
<213> ORGANISM: Sterculia foetida
<220> FEATURE:
<221> NAME/KEY: misc_feature
<223> OTHER INFORMATION: S. foetida DGAT cDNA

<400> SEQUENCE: 3
atgggggaag aaagggagga gagaaaggcg gctggacctg gacctgaacc tgggtatagg      60

```
gtattcagtg gaagagatga attcccgtcc aacatggtgc acagcgtaat agctattgcg    120
ttatggcttt ggactattca tttcaacgcc ctcttgcttc ttctctccct tatattcctg    180
ccttttccca aattccttgt ggtgttcgga tttcttttgg ttttcgtgtt tcttcctatt    240
gatcctgaca gtaaatttgg tcggcgcttg ggcaggtata tatgcaagca tctttgcagt    300
tattttccca ccactctcca cgttgaggac attcacgcct tccatcctga tcgtgcttac    360 gttttggtt atgagccaca ttcaatttgg ccaatcggag ttgttacact tgctgaactt    420
acaggtttcc tacctcttcc gaaaatgaaa gtccttgcta ccagcgttgt attctacact    480
ccatttttgc ggcatatatg gacatggttg ggtgtctcac cagctacaag gaaaactttt    540
tattccctat tggatgctgg ttatagttgt attatagtgc ctggtggagt gcaggagata    600
taccacatgg agcttggttc tgaggttgcg ttccttaggg cacgaaaagg atttgttcgc    660
atagccatgg aaaagggctg tccactggtt ccagtttttct gttttggtca gtcccatgcc    720
tacaagtggt ggaaaccaag cgggaagttg tacctgcaat tttcccgagc tatcaagttc    780
attccgatat tcttttgggg aattcttgga actcctttac cctatcaaca tccaatgcat    840
gtggtggtgg gtaaacctat tgacttgaag agaaatccac aacctactga cgaagaggtt    900
cttgaagtac atcggcaatt tgttcaagca cttcaagatc tctttgagag acacaaggct    960
cgggttggat atgctgatct tccattaaag attctttga                          999
```

<210> SEQ ID NO 4
<211> LENGTH: 332
<212> TYPE: PRT
<213> ORGANISM: Sterculia foetida
<220> FEATURE:
<221> NAME/KEY: misc_feature
<223> OTHER INFORMATION: S. foetida DGAT

<400> SEQUENCE: 4

```
Met Gly Glu Glu Arg Glu Arg Lys Ala Ala Gly Pro Gly Pro Glu
1               5                   10                  15

Pro Gly Tyr Arg Val Phe Ser Gly Arg Asp Glu Phe Pro Ser Asn Met
            20                  25                  30

Val His Ser Val Ile Ala Ile Ala Leu Trp Leu Trp Thr Ile His Phe
        35                  40                  45

Asn Ala Leu Leu Leu Leu Ser Leu Ile Phe Leu Pro Phe Ser Lys
    50                  55                  60

Phe Leu Val Val Phe Gly Phe Leu Leu Val Phe Val Phe Leu Pro Ile
65                  70                  75                  80

Asp Pro Asp Ser Lys Phe Gly Arg Arg Leu Gly Arg Tyr Ile Cys Lys
                85                  90                  95

His Leu Cys Ser Tyr Phe Pro Thr Thr Leu His Val Glu Asp Ile His
            100                 105                 110

Ala Phe His Pro Asp Arg Ala Tyr Val Phe Gly Tyr Glu Pro His Ser
        115                 120                 125

Ile Trp Pro Ile Gly Val Val Thr Leu Ala Glu Leu Thr Gly Phe Leu
    130                 135                 140

Pro Leu Pro Lys Met Lys Val Leu Ala Thr Ser Val Val Phe Tyr Thr
145                 150                 155                 160

Pro Phe Leu Arg His Ile Trp Thr Trp Leu Gly Val Ser Pro Ala Thr
                165                 170                 175

Arg Lys Thr Phe Tyr Ser Leu Leu Asp Ala Gly Tyr Ser Cys Ile Ile
            180                 185                 190
```

Val Pro Gly Gly Val Gln Glu Ile Tyr His Met Glu Leu Gly Ser Glu
            195                 200                 205

Val Ala Phe Leu Arg Ala Arg Lys Gly Phe Val Arg Ile Ala Met Glu
        210                 215                 220

Lys Gly Cys Pro Leu Val Pro Val Phe Cys Phe Gly Gln Ser His Ala
225                 230                 235                 240

Tyr Lys Trp Trp Lys Pro Ser Gly Lys Leu Tyr Leu Gln Phe Ser Arg
                245                 250                 255

Ala Ile Lys Phe Ile Pro Ile Phe Phe Trp Gly Ile Leu Gly Thr Pro
            260                 265                 270

Leu Pro Tyr Gln His Pro Met His Val Val Gly Lys Pro Ile Asp
        275                 280                 285

Leu Lys Arg Asn Pro Gln Pro Thr Asp Glu Glu Val Leu Glu Val His
290                 295                 300

Arg Gln Phe Val Gln Ala Leu Gln Asp Leu Phe Glu Arg His Lys Ala
305                 310                 315                 320

Arg Val Gly Tyr Ala Asp Leu Pro Leu Lys Ile Leu
                325                 330

```
<210> SEQ ID NO 5
<211> LENGTH: 2169
<212> TYPE: DNA
<213> ORGANISM: Sterculia foetida
<220> FEATURE:
<221> NAME/KEY: misc_feature
<223> OTHER INFORMATION: S. foetida PDAT cDNA

<400> SEQUENCE: 5
atgaccatta tggtcgccgg cggcaaggta cagaaagaag gcactttatc cggtcaatgt      60
gaacaatccc agaatcagaa ttctcagtct ctattaatga gcaaaccagt tcaaccgcag     120
agtctttata gatctcattt tgggttccaa acaatgtcgt ttttgcggcg gaggaaggta     180
acggagtcct cgaaatcctc aagctccgaa cccaacatcg aaaacgaagc ggacaagaaa     240
aaccgataca agagcccgca agaaaaacgt tatagttcga gaaatggtc gtgttgggac      300 agatgttgtt ggtacattgg ttttatgtgt tcgctgtggt ggttcttgtt gttcttatac     360
aatgcaatgc cggcttcatt cccgcaatac gtaacgcagg cgataactgg gccgttgccg     420
gacccgcctg gggttaagtt gaggaaagag ggcttgacgg tgaatcaccc ggtggtatta     480
gtgcctgggg ttgtgactgg tggacttgag ctttgggaag ggcgggagtg tgcgaaaggg     540
ttgcttggga aacgcctttg gggtggctac tttggagaac tgtataaaag acccttatgc     600
tggcttgagc acatctcact tgataatgaa actggactgg accctcctgg tataagggtc     660
aggcctgtat ctggacttgt ggcagcagat tatttcgcag caggttattt tgtttgggct     720
gttttaattg ctaatttggc tcatattggg tatgaggaaa aaacatgta tatggctgct      780 tatgattgga ggttatcttt tcagaacacg gaggtcaggg accaaacttt aaccagaata     840
aaaagtaaca tagaactctt ggtagctaca aatggtggga aaaggtagt agtccttcca      900 cattcaatgg gagtccagta ctttctgcac ttcatgaaat gggttgaagc accacctccc     960
gtgggtggtg gaggtggatc agattggtgt gctaggcaca taaaggcagt agtgaacatt    1020
ggtgcaccct ttttaggttg tccgaaatcg gtcccactgc atttttctat cgaagtcaag    1080
gatatagcga atctcaggc ttttgcacca ggttttctgg aaaagatgt acttggtctc      1140 aaaatgtttc agcatttaat gcggatgttc cgtacgtggg atgccaccag gtcaatgata    1200
```

-continued

```
ccaaaaggtg gggaaactat ctggggtggg cttgattggt cacctgaagt aggaagcttt    1260
aactctagtg cgaaaaaatt gaagaacaat agcacccata atacaggcca aaactcaaac    1320 agctatttt  gtgatatgaa aggcgtgaat tatgggagaa ttatttcatt tgggaaagat    1380
gtggctgagg cagattcctc cacaatagag agggttgatt tcagggatgc tgtaaagagc    1440
gataagcttg ccaactcaag caactgtgat gtatggatag agtatcatga attgggcaat    1500
ggagatatca aagcagttgc tgattcaaaa gtttacactg ctggatcatt tttggatctg    1560
cttcgttttg ttgccccccaa gtggatggaa cggggtgatg ctcattttc  gtatgggata    1620 gcagatgatt tggatgaccc aaagtatgaa cactacaaat attggtcaaa ccccttagaa    1680
acaaagttac caaatgctcc aaacatggaa atctactcaa tgtatggagt tggactcccc    1740
actgaaagag cttatatcta caaattaact actgccactg attgctatat tccgtttgag    1800
atagacatct cagcagaggg tggtagtgaa gattcatgtc taaaaggtgg tgttttctct    1860
gttgatggag atgaatccgt tcctgtttta agtgcaggtt tcacgtgtgc aaaagcttgg    1920
cggggtaaaa ccagattcaa tccttcaggg attcgtactt acataaggga gtacaatcat    1980 gccccctccag ctagtcttct agaaggtcga ggcacgcaaa gtggttctca tgttgatata    2040
ttggggaatt ttgctttgat tgaggatgtt atccgaatag cagcagggc  tactggtgag    2100 gacctgggtg gagatcgtgt ttattctgat atttttgaat ggtctgaaag gatcaactta    2160
aagctttag                                                            2169
```

<210> SEQ ID NO 6
<211> LENGTH: 722
<212> TYPE: PRT
<213> ORGANISM: Sterculia foetida
<220> FEATURE:
<221> NAME/KEY: misc_feature
<223> OTHER INFORMATION: S. foetida PDAT

<400> SEQUENCE: 6

```
Met Thr Ile Met Val Ala Gly Gly Lys Val Gln Lys Glu Gly Thr Leu
1               5                   10                  15

Ser Gly Gln Cys Glu Gln Ser Gln Asn Gln Asn Ser Gln Ser Leu Leu
            20                  25                  30

Met Ser Lys Pro Val Gln Pro Gln Ser Leu Tyr Arg Ser His Phe Gly
        35                  40                  45

Phe Gln Thr Met Ser Phe Leu Arg Arg Arg Lys Val Thr Glu Ser Ser
    50                  55                  60

Lys Ser Ser Ser Glu Pro Asn Ile Glu Asn Glu Ala Asp Lys Lys
65                  70                  75                  80

Asn Arg Tyr Lys Ser Pro Gln Arg Lys Arg Tyr Ser Ser Lys Lys Trp
                85                  90                  95

Ser Cys Trp Asp Arg Cys Cys Trp Tyr Ile Gly Phe Met Cys Ser Leu
            100                 105                 110

Trp Trp Phe Leu Leu Phe Leu Tyr Asn Ala Met Pro Ala Ser Phe Pro
        115                 120                 125

Gln Tyr Val Thr Gln Ala Ile Thr Gly Pro Leu Pro Asp Pro Pro Gly
    130                 135                 140

Val Lys Leu Arg Lys Glu Gly Leu Thr Val Asn His Pro Val Val Leu
145                 150                 155                 160

Val Pro Gly Val Val Thr Gly Gly Leu Glu Leu Trp Glu Gly Arg Glu
                165                 170                 175

Cys Ala Lys Gly Leu Leu Gly Lys Arg Leu Trp Gly Gly Tyr Phe Gly
```

```
            180                 185                 190
Glu Leu Tyr Lys Arg Pro Leu Cys Trp Leu Glu His Ile Ser Leu Asp
            195                 200                 205

Asn Glu Thr Gly Leu Asp Pro Pro Gly Ile Arg Val Arg Pro Val Ser
            210                 215                 220

Gly Leu Val Ala Ala Asp Tyr Phe Ala Ala Gly Tyr Phe Val Trp Ala
225                 230                 235                 240

Val Leu Ile Ala Asn Leu Ala His Ile Gly Tyr Glu Glu Lys Asn Met
            245                 250                 255

Tyr Met Ala Ala Tyr Asp Trp Arg Leu Ser Phe Gln Asn Thr Glu Val
            260                 265                 270

Arg Asp Gln Thr Leu Thr Arg Ile Lys Ser Asn Ile Glu Leu Leu Val
            275                 280                 285

Ala Thr Asn Gly Gly Lys Lys Val Val Leu Pro His Ser Met Gly
            290                 295                 300

Val Gln Tyr Phe Leu His Phe Met Lys Trp Val Glu Ala Pro Pro Pro
305                 310                 315                 320

Val Gly Gly Gly Gly Ser Asp Trp Cys Ala Arg His Ile Lys Ala
            325                 330                 335

Val Val Asn Ile Gly Ala Pro Phe Leu Gly Cys Pro Lys Ser Val Pro
            340                 345                 350

Leu His Phe Ser Ile Glu Val Lys Asp Ile Ala Asn Leu Arg Ala Phe
            355                 360                 365

Ala Pro Gly Phe Leu Glu Lys Asp Val Leu Gly Leu Lys Met Phe Gln
            370                 375                 380

His Leu Met Arg Met Phe Arg Thr Trp Asp Ala Thr Arg Ser Met Ile
385                 390                 395                 400

Pro Lys Gly Gly Glu Thr Ile Trp Gly Gly Leu Asp Trp Ser Pro Glu
            405                 410                 415

Val Gly Ser Phe Asn Ser Ser Ala Lys Lys Leu Lys Asn Asn Ser Thr
            420                 425                 430

His Asn Thr Gly Gln Asn Ser Asn Ser Tyr Phe Cys Asp Met Lys Gly
            435                 440                 445

Val Asn Tyr Gly Arg Ile Ile Ser Phe Gly Lys Asp Val Ala Glu Ala
            450                 455                 460

Asp Ser Ser Thr Ile Glu Arg Val Asp Phe Arg Asp Ala Val Lys Ser
465                 470                 475                 480

Asp Lys Leu Ala Asn Ser Ser Asn Cys Asp Val Trp Ile Glu Tyr His
            485                 490                 495

Glu Leu Gly Asn Gly Asp Ile Lys Ala Val Ala Asp Ser Lys Val Tyr
            500                 505                 510

Thr Ala Gly Ser Phe Leu Asp Leu Leu Arg Phe Val Ala Pro Lys Trp
            515                 520                 525

Met Glu Arg Gly Asp Ala His Phe Ser Tyr Gly Ile Ala Asp Asp Leu
            530                 535                 540

Asp Asp Pro Lys Tyr Glu His Tyr Lys Tyr Trp Ser Asn Pro Leu Glu
545                 550                 555                 560

Thr Lys Leu Pro Asn Ala Pro Asn Met Glu Ile Tyr Ser Met Tyr Gly
            565                 570                 575

Val Gly Leu Pro Thr Glu Arg Ala Tyr Ile Tyr Lys Leu Thr Thr Ala
            580                 585                 590

Thr Asp Cys Tyr Ile Pro Phe Glu Ile Asp Ile Ser Ala Glu Gly Gly
            595                 600                 605
```

-continued

```
Ser Glu Asp Ser Cys Leu Lys Gly Gly Val Phe Ser Val Asp Gly Asp
    610                 615                 620

Glu Ser Val Pro Val Leu Ser Ala Gly Phe Thr Cys Ala Lys Ala Trp
625                 630                 635                 640

Arg Gly Lys Thr Arg Phe Asn Pro Ser Gly Ile Arg Thr Tyr Ile Arg
                645                 650                 655

Glu Tyr Asn His Ala Pro Pro Ala Ser Leu Leu Glu Gly Arg Gly Thr
                660                 665                 670

Gln Ser Gly Ser His Val Asp Ile Leu Gly Asn Phe Ala Leu Ile Glu
        675                 680                 685

Asp Val Ile Arg Ile Ala Ala Gly Ala Thr Gly Glu Asp Leu Gly Gly
    690                 695                 700

Asp Arg Val Tyr Ser Asp Ile Phe Glu Trp Ser Glu Arg Ile Asn Leu
705                 710                 715                 720

Lys Leu
```

ENGINEERING CYCLOPROPANE FATTY ACID ACCUMULATION IN PLANTS

PRIORITY

This application claims benefit of U.S. Provisional Application No. 61/870,819, filed Aug. 28, 2013, which application is incorporated herein by reference in its entirety.

GOVERNMENT SUPPORT

This invention was made with U.S. Government support under contract number DE-AC02-98CH10886, awarded by the U.S. Department of Energy, and Grant DBI 0701919 awarded by the National Science Foundation. The U.S. Government has certain rights in the invention.

FIELD OF THE INVENTION

This invention relates to the field of agronomy and more specifically to methods for generating crop plants that produce valuable modified fatty acids for use as renewable sources industrial feedstocks. Specifically the invention herein described provides crop plants that produce increased amounts of cyclopropane fatty acids.

BACKGROUND ART

Modified fatty acids (mFAs) (also referred to as unusual or specialized fatty acids) obtained from plants have important roles as feedstock for industrial materials such as lubricants, protective coatings, plastics, inks, cosmetics, and etc. mFAs are naturally produced by a limited number of species (source plants) which are generally not readily cultivated at scale. The potential for industrial use of mFAs has led to considerable interest in exploring their production in transgenic crop plants rather than isolating, for example, a specific mFA from a specific source plant. Unfortunately, transgenic crop plants transformed with source plant genes or DNA sequences (e.g., cDNAs) encoding mFA-producing enzymes generally accumulate only modest amounts of the mFA compared to amounts accumulating in the natural source plant (Napier (2007) Ann. Rev. Plant Biol. 58:295-319). Levels of mFAs accumulating in the seeds of transformed plants rarely exceed 20% of the total seed FA whereas, for example, castor seeds naturally accumulate >90% ricinoleic acid and Tung (*Aleuites fordii*) seeds naturally accumulate >80% α-Eleostearic acid (Drexler et al. (2003) J. Plant Physiol. 160:779-802; Thelen et al. (2002) Metab. Eng. 4:12-21).

In order to elevate the content of mFAs in the engineered transgenic plants to levels approaching that found in the source plant, it is necessary to 1) optimize the synthesis of mFA (Mekhedov, et al. (2001) Plant Mol. Biol. 47:507-518) 2) minimize its degradation (Eccleston et al. (1998) Plant Cell 10:613-621); and 3) optimize its incorporation into triacylglycerol (TAG) (Bafor et al. (1990) Biochem. J. 272:31-38; Bates et al. (2011) Plant J. 68:387-399; van Erp et al. (2011) Plant Physiol. 155:683-693).

Among the modified fatty acids, cyclic FAs (CFAs) (generally cyclopropane- and cyclopropene-containing FAs (CPAs)) are desirable for numerous industrial applications. The strained bond angles of the carbocyclic ring contribute to their unique chemical and physical properties. Hydrogenation of a cyclic FA results in ring opening to produce a methyl-branched FA. Branched-chain FAs are ideally suited for the oleochemical industry as feedstocks for the production of lubricants, plastics, paints, dyes, and coatings (Carlsson et al. (2011) Eur. J. Lipid Sci. Technol. 113:812-831).

Cyclic FAs (CFAs) have been found in certain gymnosperms, Malvales (including cotton), *Litchi* and other Sapindales. They accumulate to as much as 40% in seeds of *Litchi chinensis* (Gaydou et al. (1993) J. Agri. & Food Chem. 41:886-890; Vickery (1980) J. Amer. Oil Chem. Soc. 57:87-91). *Sterculia foetida* accumulates a desaturated cyclic FA, cyclopropene FA (sterculic acid), to >60% of its seed oil.

In all cases examined, the production of a CPA begins with methyl group addition by a cyclopropane fatty acid synthase (CPS) enzyme at a carbon-carbon double bond of an unsaturated fatty acid compound. For example, the first step in the synthesis of sterculic acid is the formation of the CPA, dihydrosterculic acid (DHSA), by the CPS enzyme that transfers a methyl group from S-adenosylmethionine to C9 of the oleoyl-phospholipid followed by cyclization to form the cyclopropane ring and dehydrogenation to form the cyclopropene fatty acid, sterculic acid (Bao et al. (2002) Proc. Natl. Acad. Sci. USA 99:7172-7177; Bao et al. (2003) J. Biol. Chem. 278:12846-12853; Grogan et al. (1997) Microbiol. Mol. Biol. Rev. 61:429-441).

Because none of the known natural source plants for CPAs are suitable for commercial-scale cultivation it is desirable to create a crop plant and preferably an oilseed crop plant that accumulates high levels of CPA by expressing a heterologous CPS in the crop plant seeds. However, to date, heterologous expression of plant cyclopropane synthase coding sequences led to only 1 to 3% DHSA in transformed tobacco (K. M. Schmid, U.S. Pat. No. 5,936,139) and only ~1.0% CPA in transgenic seeds (Yu et al. (2011) BMC Plant Biol. 11:97). Thus merely expressing a cyclopropane synthase coding sequence in a crop plant is insufficient to generate a transformed crop plant to produce industrially meaningful amounts of CPAs.

As noted, and as exemplified in the results for CPA, the engineering of transgenic crop plants that accumulate commercially meaningful amounts of a modified fatty acid compound is a complex proposition requiring a refined balance of synthesis, degradation and conversion to triacylglycerol storage compounds. Mere over-expression of the "modified fatty acid synthase" or "fatty acid modifying" coding sequence has proven insufficient.

Significant efforts to achieve this balance have been devoted to generating transgenic crop plants that accumulate commercially relevant amounts of ricinoleic acid. Ricinoleic acid production has been targeted because of its well-known industrial utility and the difficulties associated with obtaining it from the seeds of castor. The combination of Smith, et al. (2003) Planta 217:507-516, van Erp, et al. (2011), and Browse, et al. (U.S. Pat. No. 8,101,818), the entire contents of all three of which are incorporated herein by reference, serves to frame the issues.

One such issue is in part described in Smith, et al. (2003) where the influence of the genetic or phenotypic background of the progenitor parent plant is considered. The authors of that work explore the effects of several parental backgrounds, including plants deficient in FAD2 activity, FAE1 activity and FAD3 activity, and combinations of these deficiencies on the net accumulation of hydroxyl-fatty acids in transgenic *Arabidopsis*.

The other issue that these works address relates to the configuration of the substrate for the fatty acid modifying enzymes. The fatty acid modifying enzymes, whether the hydroxylase or the cyclopropane synthase or other fatty acid modifying enzymes, require specific configurations of their molecular substrates. FIG. 1 of Smith, et al. (2003) notes "For convenience, fatty acids are shown as free fatty acids." (emphasis added) The fatty acid synthase/fatty acid modifying enzymes act upon their fatty acid substrate when the substrate is configured in an esterified form of one sort or another. The diagram of the options for incorporation of hydroxyl fatty acid (HFA) into HFA-TAG shown in van Erp, et al. (2011), FIG. 1, serves to point out the array of pathways, enzymes and substrate pools that participate in the desired outcome of balancing synthesis, degradation and conversion to HFA-TAG. Thus, as described in van Erp, et al. (2011) and Browse et al. (U.S. Pat. No. 8,101,818), selection of the additional activity (or activities) to be co-expressed in the prospective transgenic, mFA-producing crop plant is not a trivial undertaking. Because of the interacting and intersecting pathways, the effective combination that produces the outcome of significant accumulation of the desired mFA in the seeds (or other tissues) of the targeted crop plant cannot be predicted or foreseen. Simply stating, for example, that "co-expression of a suitable acyltransferase" (lank, et al., U.S. Pat. No. 7,723,574) would make it possible to increase accumulation of a modified fatty acid in transgenic plants does not solve the problem of how to select the suitable acyltransferase from among the numerous potential candidates.

Thus, there remains a need to produce a transgenic crop plant that accumulates commercially relevant amounts of modified fatty acids of interest and particularly in the present invention, cyclopropane fatty acids. In addition to the cyclopropane fatty acid synthase, the metabolic backgrounds of the progenitor plant, and the definition of the acyltransferase or other enzymes to be co-expressed with the cyclopropane fatty acid synthase represent aspects of the present invention.

BRIEF DESCRIPTION

Expression of cyclopropane fatty acid synthase in plants that have elevated levels of 18:1 (oleic) fatty acids (high oleate plants) compared to a wild type parent/progenitor plant results in enhancement of the accumulation of dihydrosterculic acid. Strains of progenitor plants having a fad2fae1 genotype or phenotype accumulate elevated levels of oleic acid (18:1 fatty acid) and when transformed with CPS coding sequences accumulate elevated amounts of cyclopropane fatty acids (dihydrosterculic acid) compared to the wild type parent strain.

Additional enhancement of accumulation in CPS-expressing fad2fae1 strains is achieved by co-expressing or over-expressing certain fatty acid acyl transferase genes or coding sequences. Co-expressing acyltransferase genes or coding sequences (e.g., cDNAs) from species that naturally accumulate high amounts of cyclic fatty acids is especially effective in enhancing accumulation of CPAs in transformed plants. Species of malvales, sapindales and litchi are preferred.

In one embodiment, the co-expression of the S. foetida lysophosphatidic acid acyltransferase (SfLPAT) cDNA in fad2fae1 plant strains expressing non-native cyclopropane synthase greatly enhances the accumulation of CPAs. LPAT coding sequences from other plants such as L. chinensis and cotton that accumulate high levels and moderate levels of cyclic fatty acids may also enhance accumulation in transgenic crop plants.

In additional embodiments, the co-expression of either S. foetida diacylglycerol acyl transferase (DGAT) or phospholipid diacylglycerol acyl transferase (PDAT) with non-native cyclopropane synthase in fad2fae1 plant strains significantly enhance accumulation of CPAs.

In additional embodiments, over-expression of combinations of S. foetida LPAT, DGAT and PDAT with the non-native cyclopropane synthase in fad2fae1 (high oleate) plants is contemplated to provide even further enhancement of accumulations of cyclopropane fatty acids.

It is further contemplated that co-expression of these transferases may enhance the accumulation of the CPAs as triacylglycerol (TAG) compounds.

Specific CPS genes or coding sequences (e.g., cDNAs) to be expressed in a transformed fad2fae1 plant are selected by determination of which CPS sequences result in the highest accumulation of the cyclopropane fatty acid. CPS coding sequences from cotton, Escherichia coli and other bacteria, Arabidopsis, S. foetida, L. chinensis, algae, fungi, yeast and others are candidates. The optimal CPS sequence likely depends upon the species of plant to be transformed. In one embodiment, the E. coli CPS gene was more effective than several other CPS coding sequences in elevating accumulation of cyclic fatty acids in the plants having high levels of 18:1 oleic acid.

In combination with the selection of the CPS coding sequence, selection of an appropriate acyl transferase sequence may depend upon the crop plant being modified. Acyl transferase candidates may be selected from the group consisting of lysophosphatidic acid acyl transferase (LPAT), phospholipid diacylglycerol acyl transferase (PDAT), diacylglycerol acyl transferase (DGAT).

Co-expression of cholinephosphotransferases such as phosphatidylcholine:diacylglycerol cholinephosphotransferase (PDCT), lysophosphatidylcholine tranacylase (LPCT) and gllycerophosphocholine:acyl-CoA acyltransferase (GPCAT) may also be useful for increasing amounts of mFAs in transgenic crop plants.

A desirable source of the acyl transferase coding sequence is any plant that naturally produces elevated amounts of CPAs. Particularly desirable plant sources of the acyl transferase sequences include the Malvales, the Salpindales, S. foetida, and L. chinensis. A particularly preferred acyltransferase is the lysophosphatidic acid acyl transferase (LPAT) from S. foetida (SfLPAT). Additional preferred transferases include the DGAT and PDAT of S. foetida.

BRIEF DESCRIPTION OF THE DRAWINGS

FIG. 3: Sequence of SfLPAT cDNA (SEQ ID NO. 1).

DETAILED DESCRIPTION

Genes and sequences encoding nine higher-plant cyclopropane fatty acid synthase (CPS) enzymes were expressed in fatty acid desaturase 2 (FAD2)/fatty acid elongase 1 (FAE1) deficient Arabidopsis plants (hereinafter, "fad2fae1 Arabidopsis"). Sequences for CPS enzymes from cotton, Arabidopsis and Sterculia independently expressed in the seeds of the fad2fae1 Arabidopsis resulted in an observed CPA accumulation of up to ~1%.

Expression of the *E. coli* CPS (EcCPS) gene resulted in the accumulation of up to 9.1% CPA in the seeds of fad2fae1 *Arabidopsis*. Co-expression of a *Sterculia foetida* (Sf) lysophosphatidic acid acyltransferase (LPAT) further increased CPA accumulation up to 35% in individual T1 seeds. Co-expression of EcCPS and SfLPAT results in increased accumulation of CPA in both polar lipids and TAG.

Fad2fae1 camelina plants that accumulate over 70% 18:1 fatty acid and which were created by RNAi suppression of FAD2 and FAE1 (see Nguyen et al, (2013) Plant Biotechnology 11:759-769) were used as host plants for engineering CPA production. Among four CPS sequences tested, including two from cotton (GhCPS1 and GhCPS2), one from *Sterculia* (SfCPS), and one from *E. coli* (EcCPS), only the expression of EcCPS yielded seeds with quantifiable CPA. T2 lines containing single locus of insertions of the EcCPS gene were identified and propagated to produce T3 homozygous seeds. In these T3 plant seeds, CPA accumulation reached up to approximately 10%.

Figure 4:
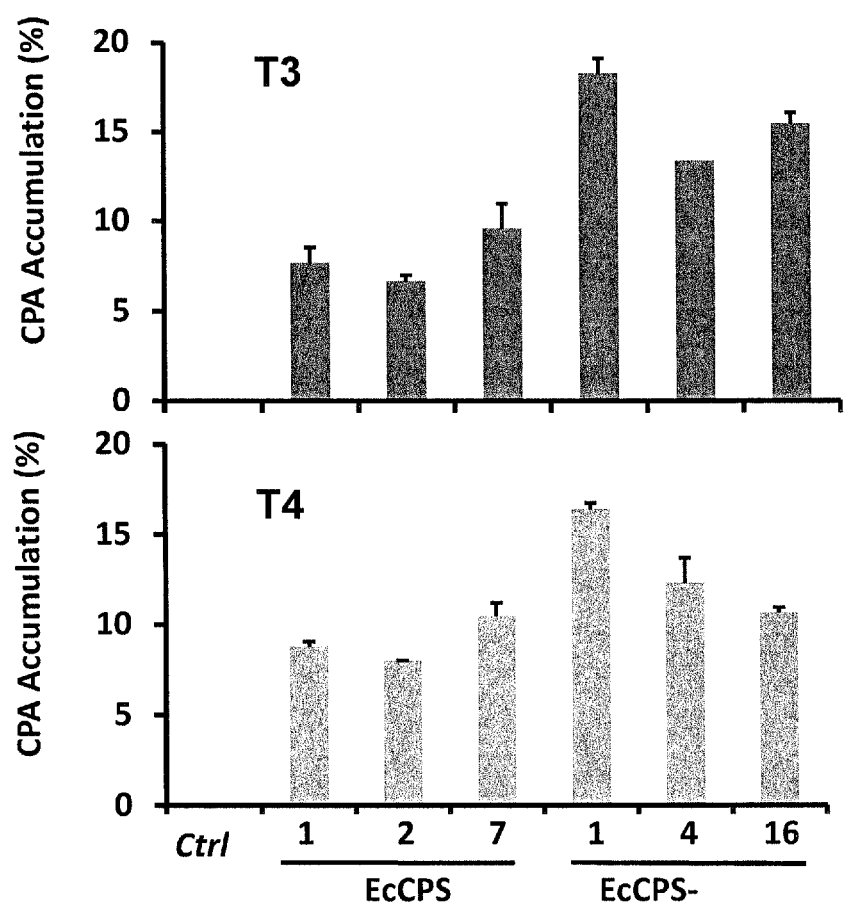
FIG. 4: Cyclopropane fatty acid accumulation in T3 and T4 camelina lines.

Co-expression of the SfLPAT cDNA sequence (SEQ ID NO. 1) along with the EcCPS gene in the T3 camelina plants yielded seeds having the highest content of dihydrosterculic acid (DHSA). Seeds of some transgenic plants accumulated up to 18.3% DHSA. Accumulation of DHSA was stabilized at about 16.4% in T4 seeds (FIG. 4). Seeds of T4 lines of EcCPS transgenic camelina accumulated up to 10.5% CPA and seeds of T4 lines of EcCPS-SfLPAT transgenic camelina accumulated CPA ranging from 10.8-16.4%. Consistent with *Arabidopsis*, co-expression of SfLPAT with EcCPS facilitates improved CPA accumulation in camelina seeds relative to the expression of EcCPS alone.

*Arabidopsis* and camelina seed germination, morphology, size and weight were affected differently by the expression of the transgenes and/or by the accumulation of elevated amounts of cyclopropane fatty acid.

*Arabidopsis* seeds with >9% CPA exhibited wrinkled seed morphology, reduced size and total oil accumulation. Seeds with >11% CPA exhibited decreased seed germination and establishment.

In contrast to EcCPS-SfLPAT transgenic fad2/fae1 *Arabidopsis*, nearly 100% of the EcCPS-SfLPAT transgenic fad2/fae1 camelina T1 seeds could germinate and develop into mature plants, although their germination in soil and early plant growth were slightly delayed compare to the untransformed seeds and compared to seeds expressing EcCPS alone. Germination of seeds on half-strength MS medium supplemented with sucrose did not alter the delay. Although delayed, the EcCPS-SfLPAT camelina plants flowered normally and produced similar amount of seeds as untransformed camelina. Transgenic camelina lines containing single loci of insertions were identified and allowed to self-fertilize to obtain homozygous individuals.

T3 camelina seeds from EcCPS lines 1, 2, 7, and EcCPS-SfLPAT lines 1, 14 and 16, planted and grown under identical conditions in soil alongside parental fad2fae1 camelina plants germinated at nearly 100% and developed into mature plants that showed normal seed yields. Thus, despite delayed germination and maturation to flowering and seed production, transgenic camelina seed, even with >12% CPA, germinated and developed successfully, in contrast to *Arabidopsis* in which germination was not observed if CPA accumulation exceeded 11-12%.

Figure 5:
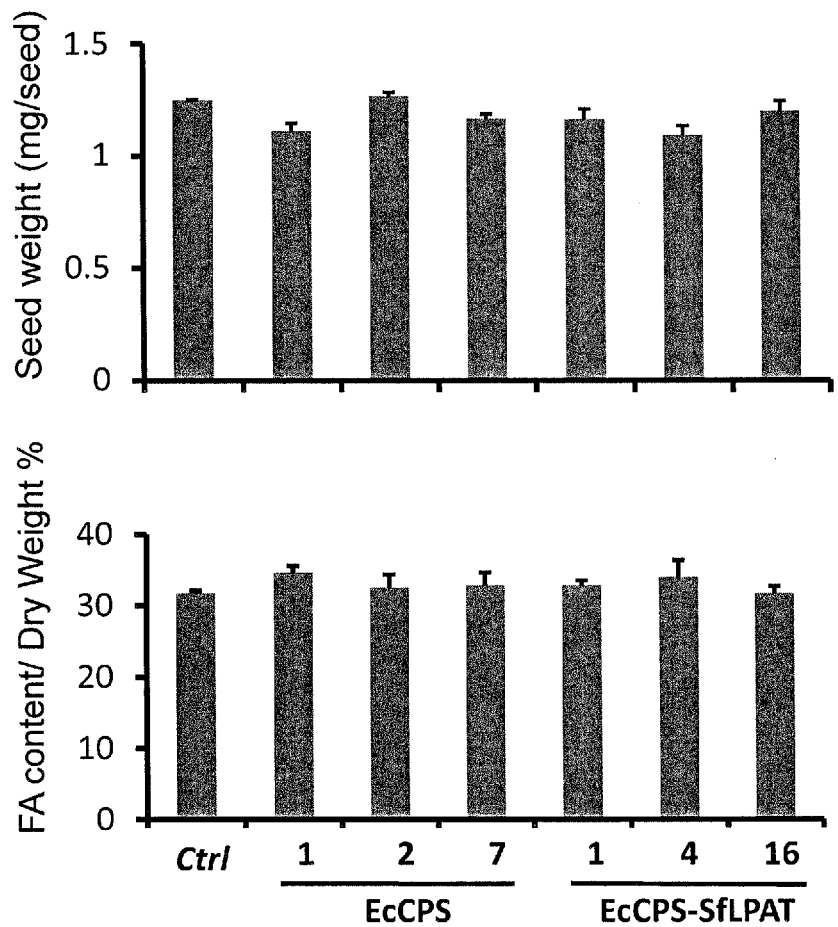
FIG. 5: Seed weight and fatty acid content in T4 camelina lines.

The co-expression of EcCPS and SfLPAT in camelina had little effect either on seed weight or total fatty acid content (FIG. 5). Parental fad2fae1 seeds weighed 1.25±0.3 mg each, whereas 5 of the 6 transgenic lines showed a decrease in mean weight. An EcCPS-SfLPAT line that accumulated the most CPA showed an approximate 7% decrease in seed weight although no definitive correlation between seed weight and CPA content was evident. One EcCPS-expressing line, EcCPS-2, showed no decrease in seed weight. The homozygous lines expressing EcCPS or co-expressing SfLPAT with EcCPS showed no decrease in total fatty acid.

It is worth noting that negative effects of accumulation of modified fatty acids (and/or the expression of non-native fatty acid modifying enzymes and non-native acyltransferases) on seed germination, morphology and size appears to vary from one species to another. In many crops, full exploitation of the exceptional accumulation of CPA by the combination of co-expression of EcCPS and SfLPAT in fad2fae1 strains will likely require additional factors to facilitate the movement of CPA from membrane lipids into TAG to produce viable seeds with CPA as a predominant FA.

Figure 1:
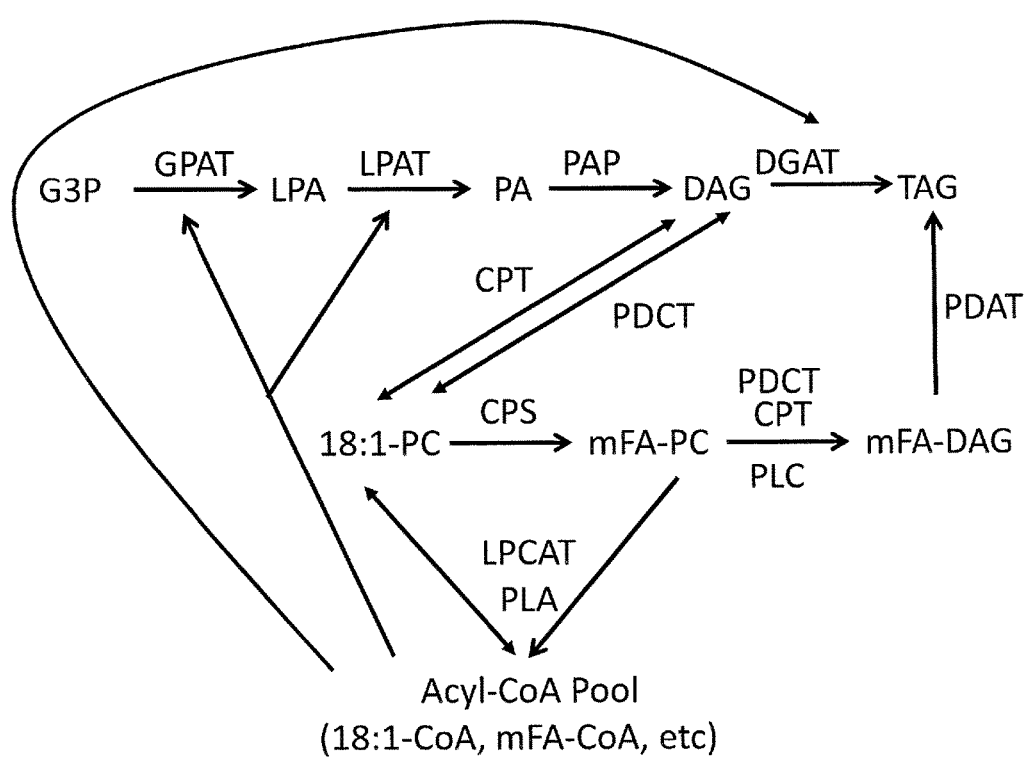
FIG. 1: A diagram of triacylglycerol (TAG) biosynthesis pathways in plants. Bates, et al. 2012, Front. Plant Sci. 3:147.

Two pathways for the biosynthesis of triacyl glycerol compounds (TAGs) exist in plants (see FIG. 1). The de novo biosynthesis from glycerol-3-phosphate and acyl-CoA occurs via the Kennedy pathway and includes three acyltransferases: Glycerol-2-phosphate Acyltransferase (GPAT), Lysophosphatidic acid Acyltransferase (LPAT or, variously, LPAAT) and Diacylglycerol Acyltransferase (DGAT) (Kennedy (1961) Fed. Proc. 20:934-940).

Alternatively acyl-CoAs can be redirected from Phosphatidyl Choline (PC) via the action of a PhosphoLipase A (PLA), by Choline PhosphoTransferase (CPT), and Phosphatidylcholine:Diacylglycerol Cholinephosphotransferase (PDCT) (Hu, et al. (2012) Plant Physiol. 158:1944-1954; Lu, et al. (2009) Proc. Natl. Acad. Sci. USA 106:18837-18842) or by Phospholipid Diacyl Glycerol Acyl Transferase (PDAT). An acyl group can be released from PC to generate lyso-PC by the back reaction of acyl-CoA:lysophosphatidylcholineacyl-transferase (LPCAT) (Stymne, et al. (1984) Biochem. J. 223:305-314; Wang, et al. (2012) Plant Cell 24:4652-4669) or a phospholipase A (Chen, et al. (2011) Plant Sci. 30:239-258).

LPAT is a pivotal enzyme controlling the metabolic flow of lysophosphatidic acid into different phosphatidic acids in diverse tissues. Membrane-associated LPAT activities, identified in bacteria, yeast, plant and animal cells, catalyze the transfer of acyl groups from acyl-CoA to lysophosphatidic acid (lysoPA) to synthesize phosphatidic acid (PA). In plants and other organisms, LPAT activities have been identified in the endoplasmic reticulum (ER) (Kim, et al. (2005) Plant Cell Physiol. 52:983-993), plasma membrane (Bursten, et al. (1991) J. Biol. Chem. 266:20732-20743) and mitochondria (Zborowski, et al. (1969) Biochim. Biophys. Acta 187:73-84). In higher plants, ER-localized LPAT plays an essential role in the synthesis of PA, a key intermediate in the biosynthesis of membrane phospholipids and storage lipids in developing seeds (Maisonneuve, et al. (2010) Plant Physiol. 152:670-684).

The results described by Nlandu Mputu, et al. (Biochimie 91:703-710 (2009)) indicate that the specificity of LPATs may cause a bottleneck limiting the incorporation of modified fatty acids (mFAs) into phosphatidic acid and then into TAG. They show that LPATs from developing seeds of flax (*Linum usitatissimum*), rape (*Brassica napus*)) and castor bean (*Ricinus communis*) preferentially incorporate oleoyl-CoA, weakly incorporate cyclopropane acyl-CoA and were unable to incorporate methyl branched acyl-CoA when presented with an equimolar mix of these potential substrates.

Enhancement of CPA accumulation in transgenic plants, including *Arabidopsis* and camelina, was achieved by co-expression of the *E. coli* CPS gene with the *Sterculia foetida*

LPAT cDNA in fad2fae1 genotypic and phenotypic strains. This underscores the utility of co-expressing the appropriate acyltransferase with mFA-synthesizing enzymes to mitigate bottlenecks in TAG formation upon the accumulation of mFA in transgenic plants.

As noted above, to make use of both pathways to the formation and accumulation of TAG compounds, it is likely that transferases operating in phosphatidyl choline acyl-editing and headgroup exchange from cyclopropane fatty acid source plants could be useful for incorporation into transgenic crop plants also co-expressing EcCPS and SfL-PAT. For example, a *Sterculia* PDCT coding sequence, homologous to the ROD1 gene of *Arabidopsis* (Lu et al., 2009), could enhance accumulation of cyclopropane fatty acids in TAG compounds via cyclopropane-fatty acid phosphatidyl choline.

Transgenic plants and their engineering by transformation of a parental/progenitor plant are well known in the art. The incorporation of additional copies of native genes or coding sequences (e.g., cDNA) and, more typically, the incorporation of non-native or heterologous coding sequences into plants and the selection of transformed progeny having and expressing such 'transformed' sequences has become routine once a transformation protocol for a particular species has emerged. For *Arabidopsis*, for example, transformants are most often created by the "floral dip" method using *Agrobacterium tumafaciens* carrying the recombinant vector or vectors. Transgenic plants that have incorporated the vectors into their genomes are selected by standard techniques. For other plants, and for specific crop plants, other methods, such as "biolistic" (gene gun) delivery and vacuum infiltration, have been developed and optimized. Such methods are used as they may be found appropriate for the particular crop plant species.

It is understood that a gene for a protein to be expressed in a transformed plant may mean either a native gene as isolated from a chromosome of the source organism or chromosome of an organelle of the organism. More typically it implies a cDNA produced from the messenger RNA encoding the protein. For example, the sequence (SEQ ID NO. 1) shown in FIG. 3 is the cDNA of the seed-expressed *S. foetida* LPAT gene exemplified here. When this cDNA gene is co-expressed with a CPS gene, additional accumulation of CPAs is achieved.

The background of the parent crop plant for embodiments of the invention can be either a genotypic or a phenotypic background. In both cases, the activities of FAD2 and/or FAE1, or both, are reduced by one means or another. Smith, et al. (2003) describe the generation of the genotypic fad2fae1 *Arabidopsis* strain from crosses of fad2 and fae1 mutant strains. Another way in which a fad2fae1 genotype could be generated is by genetic 'knockout' strategies. Variations of this technique can be used to create knockdown parental strains as well.

Phenotypic fad2fae1 strains of plants can be generated by RNAi strategies as in the case of generation of fad2fae1 RNAi camelina strains by Nguyen et al., 2013. Gene silencing by antisense and siRNA may also be used to create a plant strain that is phenotypically fad2fae1.

Crop plants may include tobacco, cotton, wheat, corn, sorghum, peanut, and oilseed crop plants including such as soybean, safflower, palm, sunflower, canola, *brassica*, cranbe and camelina. The availability of high oleate strains, such as the phenotypic and/or genotypic fad2, fae1 and/or fad2fae1 mutants, of the crop plant and the applicability of single or double mutant phenotypes and genotypes may dictate the specific crop plant targeted for modification for accumulation of cyclic fatty acids. For example, if a CPS and an LPAT enzyme activity are identified that act on C-20 mono-unsaturated fatty acid substrates, normal FAE1 levels may be preferable to a mutant deficient in FAE1 activity. If a CPS and an LPAT enzyme are identified that act on polyunsaturated fatty acids, normal FAD2 levels would likely be preferable to a mutant deficient in FAD2 activity.

Similar strategies of introduction of CPS genes and LPAT genes may be applicable to enhancing accumulation of cyclic fatty acids in algae, cyanobacteria, eubacteria, yeast or other organisms.

Co-expression of CPS genes or coding sequences with other acyl- and/or phospho-transferases, such as DGAT and PDAT, in addition to LPAT may be applied to add further enhancement and accumulation of CPAs in TAG compounds.

In particular cases, codon enhancement of the cDNAs for the various transferases may be helpful to provide sufficient levels of expression of non-native sequences in a specific crop plant.

EXEMPLIFICATIONS

Figure 2:
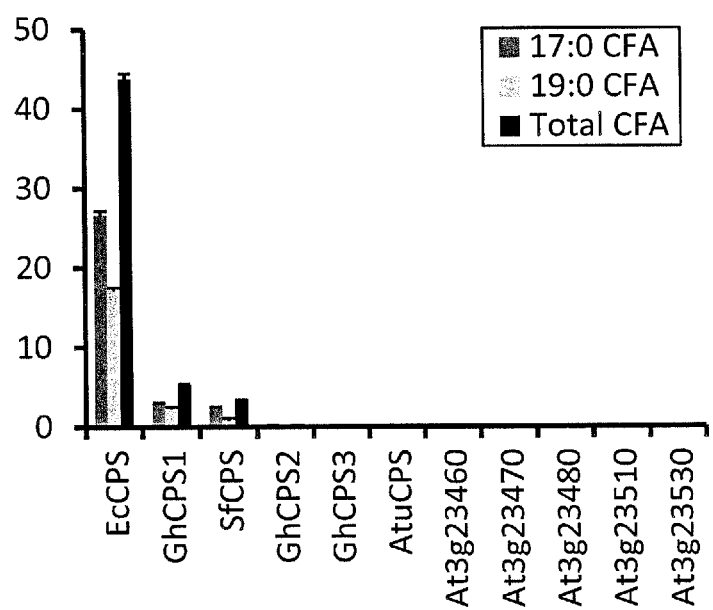
FIG. 2: Accumulation of cyclopropane fatty acids in yeast transformed with various CPS genes.

Previously, nine plant CPS coding sequences, three from cotton and one from *Sterculia*, were individually expressed in yeast. Results from this work showed that expression of GhCPS1, a CPS from cotton, led to highest levels of CPA production in yeast (5.3%) (Yu, et al., 2011). As shown in FIG. 2, the fatty acid composition of yeast expressing EcCPS showed substantial CPA accumulation. In samples from EcCPS-expressing lines two peaks corresponding to 17:0 CPA and 19:0 CPA were identified based on their mass ions (FIG. 2). Expression of EcCPS led to the accumulation of 27% 17:0 CPA and 17% 19:0 CPA yielding a total of 44% CPA accumulation, which is about 8-fold higher than that observed upon over-expression of the cotton GhCPS1 CPS sequence. The expression of *Agrobacterium* CPS and 5 putative CPS sequences from *Arabidopsis* did not yield detectable levels of CPA products. These results demonstrate the usefulness of EcCPS compared to other CPS genes with respect to their ability to convert both 16:1 and 18:1 fatty acid substrates to the corresponding 17C and 19C CPA products in yeast.

To identify a CPS gene that leads to the accumulation of higher levels of cyclopropane fatty acid in plants, CPS from *E. coli*, *Agrobacterium* and five from *Arabidopsis* were cloned and the open reading frames were transferred into plant expression vectors under the control of a seed specific phaseolin (phas) promoter and transformed into *Arabidopsis* fad2fae1 plants (Smith, et al. (2003) Planta 217:507-516). This background was chosen because its seed contains more than 80% of 18:1 monounsaturated fatty acid, the CPS substrate. Seeds expressing EcCPS yielded the highest content of dihydrosterculic acid (DHSA, 19-carbon CPA) (5.0%). No 17-carbon CPA products were detected. Expression of GhCPS1 and *Sterculia foetida* CPS led to the accumulation of at most about 1% CPA whereas expression of 5 *Arabidopsis* and two cotton orthologs (GhCPS2 and 3) resulted in no detectable accumulation of CPA. T1 fad2fae1 *Arabidopsis* seeds expressing EcCPS germinated with similar frequency to those of non-transformed seeds, and T2 lines with single locus of insertion were identified and screened for CPA production. These seeds accumulated from about 0.53% to about 5.8% CPA.

The AtLPAT2 gene sequence encoding the ubiquitous endoplasmic reticulum-located LPAT (Kim, et al. 2005) was used in a BLAST search of *Sterculia* EST sequences derived from 454 sequencing of *Sterculia* leaf and seed. A preferentially seed-expressed homologue, Ster201004_10304, which has 22 occurrences in the cotyledon and embryo of *Sterculia* developing seeds and only 5 occurrences in leaf tissue, was identified. Oligonucleotides were designed to amplify the full length cDNA, which was cloned and named SfLPAT (FIG. 3) (GenBank Accession #KC894726) (SEQ ID NO. 1). SfLPAT has a 1,164 base pair open reading frame that encodes a 387 amino acid protein with a predicted molecular weight of 43,723 Da and a theoretical pI of 9.63. The predicted amino acid sequence of SfLPAT (SEQ ID NO. 2) shows strong homology to *Litchi* LPAT (84.4%) (Thomasset et al. U.S. Patent Publication No. 2009/0271892 A1); *Arabidopsis* LPAT2 (79.2%), *Brassica* LPAT2 (79.1%) and *Arabidopsis* LPAT3 (61.9%) and weaker homology to yeast (30.5%) and *E. coli* (23.5%) LPATs.

A similar strategy was used to identify and prepare cDNAs from mRNAs for *Sterculia foetida* diacylglycerol acyltransferase (DGAT) (SEQ ID NO. 3) having the predicted amino acid sequence shown in SEQ ID NO. 4 and phospholipid diacyl glycerol acyl transferase (PDAT) (SEQ ID NO. 5) having the predicted amino acid sequence shown in SEQ ID NO. 6.

In order to test if co-expression of SfLPAT along with the EcCPS can enhance CPA accumulation, a single construct containing Phas:EcCPS and Phas:SfLPAT was transformed into the *Arabidopsis* fad2fae1 background. T1 seeds were analyzed individually for fatty acid composition. Independent T1 seeds accumulated a range of CPA content from about 3% to up to about 35% of the total fatty acid content, with 90% of tested seeds having more than 12% CPA. The co-expression of SfLPAT with EcCPS facilitates improved CPA accumulation relative to the expression of EcCPS alone.

Other studies showed that substitution of *Arabidopsis* LPAT (AtLPAT2) co-expression for SfLPAT co-expression with EcCPS was less effective in enhancing accumulation of CPA. Approximately 2-fold less CPA accumulated when AtLPAT2 was used.

Additionally, neither co-expression of SfLPAT nor co-expression of AtLPAT2 with the *Sterculia* cyclopropane fatty acid synthase (SfCPS) was as effective as co-expression with the *E. coli* CPS. The combination of SfCPS and SfLPAT was more than twice as effective as the combination of SfCPS and AtLPAT2. The combination of EcCPS with SfLPAT was 2.5- to 3-fold more effective than the combination of SfCPS and SfLPAT and about 2-fold more effective than the combination of EcCPS and AtLPAT2. Thus for accumulation of cyclopropane fatty acids in the seeds of fad2fae1 strains of plants a preferred combination is the co-expression of the *E. coli* cyclopropane fatty acid synthase with the *Sterculia foetida* LPAT.

Only approximately 30% of the EcCPS-SfLPAT T1 *Arabidopsis* seeds germinated and were able to develop into mature plants, compared to close to 100% for seeds expressing EcCPS alone. The remaining non-viable seeds showed no penetration of the seed coat by the radical suggesting a failure of germination rather than establishment. Transgenic lines containing single loci of insertion were identified and allowed to self-fertilize to obtain homozygous individuals. The fad2fae1 T2 seeds containing EcCPS and SfLPAT that accumulated low levels of CPA, along with fad2fae1 seeds containing only the EcCPS exhibited close to 100% germination rates as did the untransformed fad2fae1 seeds. In contrast, T2 fad2fae1 seeds co-expressing EcCPS-SfLPAT that contained higher than 11.5% CPA exhibited reduced germination rates even with the supplement of 1% (w/v) sucrose in the media. The results suggest that elevated accumulation of CPA rather than the presence of SfLPAT was responsible for the failure to germinate.

Five individual T3 plants from three EcCPS lines and three EcCPS-SfLPAT lines were grown along with parental fad2fae1 plants under identical conditions. There were no discernible morphological or developmental differences between transformed and non-transformed plants. There were no significant differences in flowering time, seed development or seed numbers. EcCPS T4 homozygous transgenic seeds yielded about 4.7-9.1% CPA, and the progeny of EcCPS-SfLPAT-expressing seeds accumulated CPA ranging from about 10.8-13.3%.

FA from mature seeds was trans-esterified and quantified via gas chromatography with the use of internal standards. Total seed fatty acid content of untransformed fad2fae1 was 6.45±0.61 μg. The three homozygous lines expressing EcCPS showed no significant differences from the parental line, whereas lines coexpressing SfLPAT with EcCPS resulted in a significant decrease of 18% in total fatty acid. In addition to FA content, seed weights were also determined. Parental fad2fae1 *Arabidopsis* seeds weighed 20.0±1.24 μg and T4 seeds of EcCPS expressing lines showed no significant difference, whereas equivalent lines co-expressing EcCPS and SfLPAT showed a significant decrease in seed weight of up to 11%, with the largest decreases occurring in lines accumulating the most CPA.

In *Arabidopsis*, most mFA in TAG originate from the PC pool (Bates et al., 2009). Consistent with this, the substrate for *Sterculia* CPS, is 18:1 at the sn-1 position of PC (Bao, et al., 2003). It was found that CPA accumulates at 15-18% in the polar lipid fraction of EcCPS-expressing *Arabidopsis* lines that accumulate 5-9% CPAs in the seed oil at maturity. In order to investigate whether the expression of SfLPAT influences the amount of CPA in the polar lipids, the CPA content of polar lipid and TAG of EcCPS- and EcCPS-SfLPAT-expressing seeds was analyzed. CPA accumulation in polar lipids and in TAG increased when EcCPS was co-expressed with SfLPAT.

When the *E. coli* CPS was expressed in a fad2fae1 RNAi strain of camelina (Nguyen, et al. (2013)), an enhancement of CPA accumulation was observed. When EcCPS was co-expressed with SfLPAT, the accumulation of CPS was additionally enhanced, with CPA being more than 15% of the total fatty acid in T3 seeds of the transgenic camelina. The germination of the seeds of EcCPS-SfLPAT-expressing camelina was normal as were plant growth and seed setting. However the seeds of these plants were slower to establish. It appears that for engineering cyclopropane fatty acid accumulation in a crop plant, a high oleate genotype or phenotype such as the fad2fae1 phenotypic and/or genotypic strains of camelina and *Arabidopsis* exemplified here are preferable.

Co-expression of the *E. coli* cyclopropane synthase with *S. foetida* DGAT (SfDGAT) or PDAT (SfPDAT) in fad2fae1 camelina also enhanced the accumulation of CPA. CPA accumulation in T1 seeds increased from 6.2% for plants expressing only EcCPS, to 13.9% for those expressing both EcCPS and SfDGAT, to 15.8% for plants expressing both EcCPS and SfPDAT.

A preferred embodiment is a transgenic plant that accumulates elevated amounts of cyclopropane fatty acids. The preferred transgenic plant is a plant that expresses a non-native cyclopropane fatty acid synthase such as that encoded by the *E. coli* CPS gene and also expresses a sequence encoding a lysophosphatidic acid acyltransferase from a plant that normally accumulates high amounts of cyclopropane fatty acids such as the *S. foetida* LPAT cDNA of FIG. 3 (SEQ ID NO. 1).

Additional preferred embodiments include transgenic plants that expresses a non-native cyclopropane fatty acid synthase such as that encoded by the *E. coli* CPS gene and also express a sequence encoding either or both of a diacylglycerol acyltransferase (DGAT) or a phospholipid diacyl glycerol acyltransferase from a plant that normally accumulates high amounts of cyclopropane fatty acids such as the *S. foetida* DGAT and PDAT (SEQ ID NO. 3 and 5, respectively).

Each of the cDNA sequences for SfLPAT, SfDGAT and SfPDAT may be codon optimized for expression in individual crop plants for additional enhancement of CPA accumulation for the specific crop plant.

An additional embodiment includes a transgenic plant that expresses a non-native cyclopropane fatty acid synthase such as that encoded by the *E. coli* CPS gene in combination with an LPAT, a DGAT and/or a PDAT from a plant that normally accumulates high amounts of cyclopropane fatty acids.

A preferred transgenic plant that accumulates elevated amounts of cyclopropane fatty acids is one that accumulates the CPA in its seeds.

In a seed of a preferred transgenic plant that accumulates CPA in seeds, the percentage of CPA to total FA in the seed is from about five percent (5%) to about sixty percent (60%) CPAs and preferably from about ten percent (10%) to about forty percent (40%) wherein "about" refers to an actual value within one to three percentage points of the stated value.

Individual progeny plants of such preferred transgenic plants that accumulate CPA in their seeds may exhibit a range in the levels of accumulation of CPA in their seeds. The seeds of a particular progeny strain may exhibit a seed-to-seed range of CPA accumulation. In each case, accumulation levels that are preferred are from about five percent (5%) to about sixty percent (60%) of the total fatty acid.

EXEMPLIFICATION MATERIALS AND METHODS

Vector Construction:

For expression in yeast, CPS from *E. coli* and full length cDNAs of CPSs from *Agrobacterium, Sterculia,* cotton and *Arabidopsis* were amplified and cloned into yeast expression vector pYES2 by restriction of SacI and EcoRI. For expression in plants, *E. Coli* CPS was amplified from *E. coli* strain K-12 (Substr. MG1655) using primers ECPS-5'PacI and ECPS-3'XmaI and cloned into pDsRed plant expression vector (Pidkowich, et al. (2007) Proc. Natl. Acad. Sci. USA 104:4742-4747) to form pPhasECPS. Another expression cassette of *E. coli* CPS was constructed using overlap-extension PCR (Horton, et al. (1990) Biotechniques 8:528-535). Overlapping fragments of phaseolin promoter (Pidkowich, et al. 2007), *E. coli* CPS and phaseolin terminator were amplified in separate PCR reactions using appropriate primer pairs. The PCR products were gel purified and assembled in a PCR reaction primed with terminal primers Phas5'EcoRI and Phas3'EcoRI, and cloned into the pPhasECPS vector with the EcoRI restriction site. Further restrictions screen the p2PhasECPS in which the two set of promoters are in the same direction. *Sterculia* LPAT was amplified from native plant. *Sterculia* LPAT was further cloned into p2PhasECPS through restriction of Pac I and XmaI. The *Sterculia* DGAT and PDAT cDNAs were amplified and cloned similarly.

Plant Growth Conditions and Transgenic Analyses:

Developing seeds and leaves of *S. foetida* were collected from Montgomery Botanical Center (Miami, Fla.). The seed coats were removed and the cotyledons and embryos were frozen with liquid nitrogen and stored at −80° C. for RNA extraction and lipid analysis.

*Arabidopsis* plants were grown in walk-in growth chambers at 22° C. using a 16 h photoperiod. Binary vectors were introduced into *Agrobacterium tumefaciens* strain GV3101 by electroporation and were used to transform *Arabidopsis* via the floral dip method (Clough, et al. (1998) Plant J. 16:753-743) and camelina via vacuum infiltration (Lu, et al. (2008) Plant Cell Rep. 27:273-278). Seeds of transformed plants were screened under fluorescence emitted upon illumination with green light from a X5 LED flashlight (Inova) in conjunction with a 25A red camera filter (Pidkowich et al. 2007).

Camelina plants were grown in walk-in-growth chambers at 22° C. with a 16 h photoperiod. Binary vectors were introduced into *Agrobacterium tumefaciens* strain GV3101 and transferred into camelina by *agrobacterium*-mediated inoculation of camelina plants at early flowering stage along with a vacuum infiltration procedure (Lu C., et al. 2008 Plant Cell Rep. 27:273-278). Seeds of transformed plants were screened for fluorescence emitted upon illumination with green light from a X5 LED flashlight (Inova) in conjunction with a 25A red camera filter as previously described by Pidkowich et al., 2007.

RNA Extraction and Reverse Transcription:

RNA from *Sterculia* leaf and seeds at different development stages were extracted according to Schultz, et al. (Proc. Natl. Acad. Sci. USA (1996) 93:8771-8775). RNA quality and concentration were determined by gel electrophoresis and Nanodrop spectroscopy. Reverse transcription (RT) was carried out using the QuanTect Reverse Transcription Kit (Qiagen).

Fatty Acid Analyses:

Yeast culture, expression and fatty acid analyses were carried out as described by Broadwater et al. (J. Biol. Chem. (2002) 277:15613-15620). Lipids were extracted in methanol/chloroform (2:1) from seeds and heptadecanoic acid was added as an internal standard. The isolated lipid was methylated in 1% sodium methoxide at 50° C. for 1 hr and extracted with hexane. Fatty acid methyl esters (FAMEs) from single seeds were prepared by incubating the seed with 30 μL 0.2M trimethylsulfonium hydroxide in methanol (Butte, et al. (1982) Anal. Lett. 15:841-850). Lipid profiles and acyl group identification were analyzed on a Hewlett Packard 6890 gas chromatograph equipped with a 5973 mass selective detector (GC/MS) and Agilent J&W DB 23 capillary column (30 m×0.25 μm×0.25 μm). The injector was held at 225° C. and the oven temperature was varied from 100-160° C. at 25° C./min, then to 240° C. at 10° C./min. The percentage values were converted to mole percent and presented as a mean of at least three replicates.

CPS Distribution in the TAG:

Total lipids were extracted from 20 seeds of each T4 line by homogenizing in 500 μL of methanol:chloroform:formic acid (20:10:1 vol/vol). The organic solvent was extracted with 250 μL of 1 M KCl, 0.2 M $H_3PO_4$ twice. The organic phase was dried under $N_2$ and suspended in hexane. Lipids were separated by TLC with hexane:diethylether:acetic acid (80:20:1, vol/vol). Internal standard heptadecanoic acid was added to each fraction and fatty acid methyl esters (FAMEs)

were prepared with 1 mL of methanol:HCl at 90° C. for 1 hr and extracted with hexane. FAMEs were quantified by GC-MS, as previously described (Yu et al. 2011).

It will be evident to those skilled in the art that methods for enhancing accumulation of fatty acids in vegetative tissues of plants may be combined with the teachings herein to enhance accumulation of specialized fatty acids in those vegetative plant tissues.

What is claimed is:

1. A transgenic plant comprising higher levels of oleic acid than a wild type plant wherein said transgenic plant is a fad2fae1 plant that expresses *Escherichia coli* cyclopropane synthase and *Sterculia foetida* diacylglycerol acyltransferase (DGAT) and accumulates elevated amounts of cyclopropane fatty acids, wherein the transgenic plant is an oilseed crop plant selected from the group consisting of soybean, safflower, sunflower, canola, palm, *Brassica*, Cranbe and Camelina.

2. The transgenic plant of claim 1 that accumulates cyclopropane fatty acids in its seed.

3. The seed of the transgenic plant of claim 1 wherein the cyclopropane fatty acids comprise between about five percent (5%) and about sixty percent (60%) of the total seed fatty acid.

4. The seed of the transgenic plant of claim 1 wherein the cyclopropane fatty acids comprise between about ten percent (10%) and about forty percent (40%) of the total seed fatty acid.

5. A method producing cyclopropane fatty acids in an oilseed crop plant, the method comprising transforming fad2fae1 plant having higher levels of oleic acid than a wild type plant with a construct comprising a nucleic acid sequence encoding an *Escherichia coli* cyclopropane synthase and a nucleic acid sequence encoding a *Sterculia foetida* diacylglycerol acyltransferase (DGAT), wherein the oilseed crop plant accumulates elevated amounts of cyclopropane fatty acids, wherein the transgenic plant is an oilseed crop plant selected from the group consisting of soybean, safflower, sunflower, canola, palm, *Brassica*, Cranbe and Camelina.

6. The method of claim 5, wherein the transgenic plant accumulates cyclopropane fatty acids in its seed.

7. The method of claim 5, wherein the cyclopropane fatty acids comprise between about five percent (5%) and about sixty percent (60%) of the total seed fatty acid.

8. The method of claim 5 wherein the cyclopropane fatty acids comprise between about ten percent (10%) and about forty percent (40%) of the total seed fatty acid.

* * * * *